United States Patent
Franks et al.

(10) Patent No.: US 6,426,210 B1
(45) Date of Patent: *Jul. 30, 2002

(54) STORAGE OF MATERIALS

(75) Inventors: Felix Franks; Ross Henry Hatley, both of Cambridge; Sheila Frances Mathias, Swaffham, all of (GB)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/317,779

(22) Filed: May 24, 1999

Related U.S. Application Data

(63) Continuation of application No. 08/241,457, filed on May 11, 1994, now Pat. No. 5,928,469.

(30) Foreign Application Priority Data

Jun. 26, 1991 (GB) .............................................. 9113798
Apr. 9, 1992 (GB) .............................................. 9207839

(51) Int. Cl.$^7$ ................................................. C12N 1/04
(52) U.S. Cl. ...................... 435/260; 435/188; 530/345; 159/4.01; 424/93.1; 424/93.4; 424/93.45
(58) Field of Search ................................ 435/260, 188; 530/345; 159/4.01; 424/93.1, 93.45, 94.1

(56) References Cited

U.S. PATENT DOCUMENTS

| | | | |
|---|---|---|---|
| 125,714 A | * | 4/1872 | Allen |
| 586,504 A | * | 7/1897 | Maresch |
| 1,855,591 A | | 4/1932 | Wallerstein |
| 2,648,609 A | | 8/1953 | Wurster |
| 3,202,731 A | | 8/1965 | Grevenstak et al. |
| 3,300,474 A | | 1/1967 | Flodin et al. |
| 3,312,803 A | | 4/1967 | Dame, Jr. et al. |
| 3,413,198 A | | 11/1968 | Deutsch |
| 3,456,050 A | | 7/1969 | Rieckmann et al. |
| 3,480,468 A | | 11/1969 | Carletti et al. |
| 3,540,927 A | | 11/1970 | Niim et al. |
| 3,554,767 A | | 1/1971 | Daum et al. |
| 3,554,768 A | | 1/1971 | Feldman |
| 3,617,302 A | * | 11/1971 | Collins |
| 3,620,776 A | | 11/1971 | Mishkin et al. |
| 3,666,496 A | | 5/1972 | Honey et al. |
| 3,764,716 A | | 10/1973 | Rainwala et al. |
| 3,971,852 A | | 7/1976 | Brenner et al. |
| 4,109,019 A | | 8/1978 | Moore |
| 4,157,386 A | | 6/1979 | La Rochelle |
| 4,294,624 A | | 10/1981 | Veltman |
| 4,372,942 A | | 2/1983 | Cimiluca |
| 4,423,079 A | | 12/1983 | Kline |
| 4,423,086 A | | 12/1983 | Davos et al. |
| 4,533,552 A | | 8/1985 | Kawamata |
| 4,551,329 A | | 11/1985 | Harris et al. |
| 4,587,267 A | | 5/1986 | Drake et al. |
| 4,617,272 A | | 10/1986 | Kirkwood et al. |
| 4,741,872 A | | 5/1988 | De Luca et al. |
| 4,749,575 A | | 6/1988 | Rotman |
| 4,753,790 A | | 6/1988 | Silva et al. |
| 4,762,719 A | | 8/1988 | Forester |
| 4,820,534 A | | 4/1989 | Salieb et al. |
| 4,830,858 A | | 5/1989 | Payne et al. |
| 4,847,090 A | | 7/1989 | Della Posta et al. |
| 4,849,225 A | | 7/1989 | Mitsuhashi et al. |
| 4,855,157 A | | 8/1989 | Tashiro et al. |
| 4,863,865 A | | 9/1989 | Franks |
| 4,873,085 A | | 10/1989 | Fuisz |
| 4,891,319 A | | 1/1990 | Roser |
| 4,898,781 A | | 2/1990 | Onouchi et al. |
| 4,910,135 A | | 3/1990 | Tischer et al. |
| 4,919,962 A | | 4/1990 | Arora et al. |
| 4,963,359 A | | 10/1990 | Hasiwanter et al. |
| 4,985,252 A | | 1/1991 | Jung et al. |
| 4,997,654 A | | 3/1991 | Corsello et al. |
| 5,124,162 A | | 6/1992 | Boskovic et al. |
| 6,071,428 A | * | 6/2000 | Franks |

FOREIGN PATENT DOCUMENTS

| | | |
|---|---|---|
| BE | 902257 | 8/1985 |
| DE | 159826 | 4/1905 |

(List continued on next page.)

OTHER PUBLICATIONS

Klech et al., Journal of Pharmaceutical Sciences, vol. 79, No. 11, pp. 999–1004, Nov. 1990.* van de Beek et al., Neth. Milk Dairy Journal, vol. 23, pp. 46–54, 1969.*

Vipin Dhirajlal Shah, "The Spray Drying of Enzyme Rennin," Thesis 1963.

Modes of Stabilization of a Protein by Organic Solutes during Desiccation; John F. Carpenter and John H. Crowe, Department of Zoology, University of California, Davis, California Cyrobiology 25 pp. 459–470 (1988).

Principles of "Cryostabilization" Technology from Structure/Property Relationships of Carbohydrate/Water systems—A Review, Harry Levine and Louise Slade, Nabisco Brands, Inc., Corporate Technology Group, Cryoletters 9k pp. 21–63 (1988).

(List continued on next page.)

*Primary Examiner*—Francisco Prats
*Assistant Examiner*—Susan D. Coe
(74) *Attorney, Agent, or Firm*—Susan T. Evans; Felissa H. Cagan; Stephen L. Hurst

(57) ABSTRACT

Materials which are not themselves storage-stable at room temperature are made suitable for storage by mixing them with a carrier substance and spray drying the resulting mixture so as to form particles containing both the material and the carrier substance in which the carrier substance is in an amorphous, i.e. glassy or rubbery, state. Formation of such a composition greatly enhances stability. The material stored may be a biological material such as an enzyme, the components of a chemical reaction such as reagents for carrying out an assay, or even viable biological cells.

61 Claims, 1 Drawing Sheet

FOREIGN PATENT DOCUMENTS

| | | |
|---|---|---|
| DE | 1812574 | 6/1970 |
| DE | 2415159 | 9/1975 |
| DE | 3141498 | 4/1983 |
| DE | 161072 A | 9/1984 |
| EP | 0 111 216 | 6/1984 |
| EP | 0140 489 | 5/1985 |
| EP | 0229 810 B1 | 7/1987 |
| EP | 0 297 887 | 1/1989 |
| EP | 0383569 * | 2/1990 |
| EP | 0366303 | 5/1990 |
| EP | 223221 | 4/1992 |
| EP | 244771 | 12/1992 |
| EP | 252750 | 3/1993 |
| ES | 8403520 | 6/1984 |
| GB | 1288094 | 9/1972 |
| GB | 147775 | 6/1977 |
| GB | 2126588 | 3/1984 |
| JP | 095885 A | 6/1984 |
| JP | 70-12153 B | 7/1995 |
| RU | 883174 | 11/1981 |
| WO | WO 86/00336 | 1/1986 |
| WO | WO 86/04095 | 7/1986 |
| WO | WO 87/00196 | 1/1987 |
| WO | WO 87/05300 | 9/1987 |
| WO | WO 89/06542 | 7/1989 |
| WO | WO 90/05182 | 5/1990 |

OTHER PUBLICATIONS

The Glassy State and Survival of Anyhydrous Biological Systems, Michael J. Burke, pp. 358–363, (1986) Appendix D of Membranes, Metabolism, & Dry Organisms.

Use of Lyoprotectants in the Freeze–Drying of a Model Protein, Ribonuclease, Michael W. Townsend and Patrick P. DeLuca, Journal of Parenteral Science & Technology, 42 pp. 190–199 (1988).

Some Physico–Chemical Properties of Lactose, B. L. Herrington, J Dairy Science, 17, pp. 501–519, (1934).

The Glassy State in Certain Sugar–Containing Food Products, G.W. White and S. H. Cakebread, J Food Technol. 1 pp. 73–82 (1966).

Loss of Structure in Freeze–dried Carbohydrates Solutions: Effect of Temperature, Moisture Content and Composition, Spryros Tsourouflis, James M. Flink, and Marcus Karel, J Sci Fd–Agric 27, pp. 509–519 (1976).

Structural Stability of Intermediated Moisture Foods—A New Understanding, Louis Slade and H. Levine, Food Structure, its Creation and Evaluation, Blanshard and Mitchell, pp. 115–180 (1988).

The Nature of the Glassy State and the Behavior of Liquids at Low Temperatures, Kauzmann Chem Rev 43, pp. 219–227 (1948).

A Polymer Physico–Chemical Approach to the Study of Commercial Starch Hydrolysis Products (SHPs), Harry Levine and Louise Slade, Carbohydrate Polymers, 6 pp. 213–244 (1986).

Stabilization of Phosphofructokinase during Air–Drying with Sugars and Sugar/Transition Metal Mixtures, John F. Carpenter, Beth Martin, Lois M. Crowe, and John H. Crowe, Cryobiology, 24 pp. 455–464 (1987).

Thermostability of Enzyme in the Three–dimensional Network of Polysaccarhide Chains, Z. Schneider, A. Stroinski and J. Pawelkiewiz, Bulletin de L'Acad. Polonnaise des Sciences DX1,5, pp. 203 and 204 (1968).

The Condense Chemical Dictionary, Seventh Edition, Arthur and Elizabeth Rose, Reinhold Publishing Corporation, p. 448 (1961).

Walter Relations of Foods, R.B. Duckworth, Editor, Academic Press, p. 648 (1975).

The New Encyclopedia Britannica, vol. 16, Encyclopedia Britannica, Inc., p. 476–479 (1985).

Hydration–induced Conformational and Flexibility Changes of Lysozyme at Low Water Content, P.L. Poole and J.L. Finney, Int J. Biol. Macromol., 5 pp. 308–310 (1983).

Sequential Hydration of a Dry Globular Protein, P.L. Poole and J.L. Finney, Biopolymers, 22 pp. 255–260 (1983).

Protein Hydration and Enzyme Activity: The Role of Hydration–Induced Conformation and Dynamic changes in the Activity of Lysozyme, J.L. Finney and P.L. Poole, Comments Mol Cell Biophys, 2 pp. 129–151 (1984).

Labuza et al., Biotechnology & Bioengineering, vol. XII, pp. 135–140, (1970).

Josic, Lebenson, Wiss U. Technol., vol. 15, pp. 5–14, (1982).

ABD El–Gawal et al., Egyptian J. Dairy Sci., vol. 17, pp. 273–281, (1989).

Peri et al., Lebenson—Wiss U. Technol., vol. 7, No. 2, pp. 76–81, (1974).

Ijima et al., Cryobiology, vol. 10, pp. 379–85, (1973).

Annear, Austral. J. Exp. Biol., vol. 36, pp. 211–222, (1958).

Flink, "Structure and Structure Transitions in Dried Carbohydrate Materials," Phys. Prop. of Fools, pp. 473–521, (1983).

Uedaira et al., Bulletin of the Chemical Society of Japan, vol. 53, p. 2451–5, (1980).

Okura Seiyaku, Abstract—Japanese Patents Gazette—Week 8604—Section Chemical J6 0244–288–A, 1986.

Fuji Sieu, Abstract—Japanese Patents Gazette—Week 8750—Section Chemical J6 2255–434–A, 1988.

Abstract—Japanese Patents Gezette—Week 8746—Section Chemical—Amano Pharm, KK, 1988.

Gendler et al., J. of Medicinal Chem, 24, pp. 33–38, 1981.

Malik, J. Microbiological Methods, vol. 12, pp. 125–1342, (1990).

Chopin, Can. Journal Microbiology, vol. 23, pp. 716–20, (1977).

Tertyshry et al., Microbiology J., pp. 49–52, (1988).

Dielectric Studies of Protein Hydration and Hydration–induced Flexibility, Bone and Pethig, J. Mol. Biol., 181 pp. 323–326, (1985).

Lyophilization of Biotechnology Products, Arno T. P. Skrabanaja, Andre L. J. De Meere, Rein A. De Ruiter, and Piet J.M. Van Den Detelaar, PDA Journal, 48–6 pp. 311–317 (1994).

BioPharm, Roser, Biopharm, pp. 49–53, Sep. 1991.

Developments in Biological Standardization, Pikal and Sah International Symposium on Biological Product Freeze–Drying and Formulation Bethesda, USA, 74 pp. 165–170 (1991).

Green and Angell, J. Phys. Chem, 89, 2880 (1989).

Another View of Trehalose for Drying and Stabilization Biological Materials, Levine and Slade, BioPharm, 1992.

The Crystallisation of Hydrates From Amorphous Carbohydrates, Barry J. Aldous, Anthony D. Auffret, and Felix Franks, Cryo–Letters, 16 pp. 181–186 (1995).

Roos—Carbohydrate Research, 238, 38–49 (1993).

Chemical Abstract CA 93(23): 219324n, 1980.

Chemical Abstract CA 106(14):10356–76, 1987.

Metwally et al., Egyptian J. of Dairy Sci., vol. 17, pp. 35–43, (1989).

Kim et al., J. Food Science, vol. 55, pp. 1009–1010 + 1048, (1990).

Prajapati et al., Aust. J. Dairy Technology, pp. 17–21, Mar./Jun. 1987.

Hatley et al., Biotechnology & Applied Biochemistry. vol. 11, pp. 367–370, 1989.

Polinsky et al., Proc. Natl. Acad. Sci. USA, vol. 72, No. 9, pp. 3310–3314., 1975.

Slade et al. "Non–Equilibrium Behaviours of Small Carbohydrate Water Systems" Pure and Applied Chem. vol. 60, No. 12, pp. 1841–1864., 1988.

Hatley et al. Process Biochemistry, pp. 169–172. Dec. 1987.

* cited by examiner

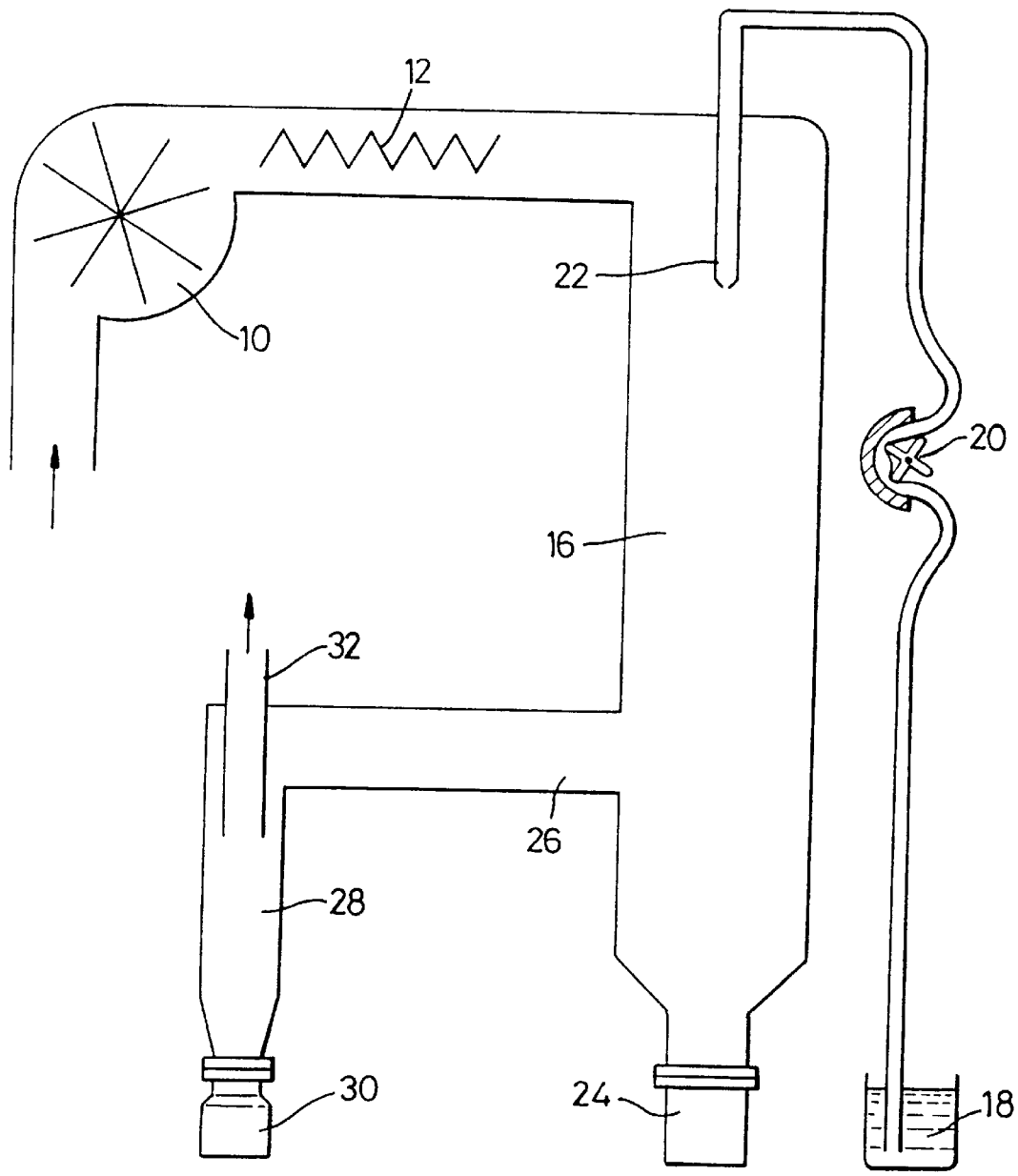

STORAGE OF MATERIALS

This application is a continuation of U.S. application Ser. No. 08/241,457, filed on May 11, 1994, now U.S. Pat. No. 5,928,469, and claims the foreign priority benefits under U.S.C. §119 of Great Britain Patent Application No. 9113798.4, filed Jun. 1991 and of Great Britain Patent Application No. 9207839.3, filed Apr. 9, 1992.

This invention relates to the stabilisation and storage of materials. The principal envisaged field of application is materials employed in the biochemical field and some pharmaceuticals.

A few biologically active materials (e.g. some proteins) are sufficiently stable that they can be isolated, purified and then stored in solution at room temperature. For most materials however this is not possible and some more elaborate form of stabilisation/storage procedure must be used.

As discussed in our co-pending European application published as EP-A-383569 a number of storage techniques are known but are not universally applicable to materials which give rise to a storage problem.

That pending application discloses the storage of materials by incorporating them into a water-soluble or water-swellable substance which is in an amorphous, glassy or (much less preferably) rubbery state.

That application discloses the preparation of storable compositions by preparing a solution of the substance(s) to be stored and a water-soluble or swellable substance, then evaporating water from the solution at room temperature or with some heating. Temperatures of 37° C. and 60° C. are exemplified. The solutions were simply held in a stationary container during drying.

It is of course considered prudent to minimise the application of heat when drying a material which is not particularly stable. Freeze drying is a prime example of this.

Spray drying is a known process for drying a solution or suspension to a solid, particulate form. The process entails delivering the solution or suspension into a flow of pre-heated gas, usually air, whereupon water rapidly evaporates from the droplets. It is widely used in the manufacture of detergent powders and in that field it is well known that certain materials are not stable to spray-drying conditions.

Spray drying has been used to kill microbial cells, for instance in dairy products as disclosed by A. Chopin et al, Can J. Microbiol 23, 716 (1977). EP-A-366303 discloses the use of spray drying to dry a cell composition with the intention that the cells will be killed but cell components such as enzymes will be recoverable from the dried composition. Spray drying has been used in attempts to dry microbial cells to a state of suspended animation from which viable cells can be recovered, but even in a relatively favourable case losses of 97% were recorded after 30 days storage at room temperature as disclosed by I. A. Abd el Gawad et al Egyptian Journal of Dairy Science, 17 273 (1989).

Surprisingly, we have now found that spray drying can be used to make storable compositions by drying mixtures of the material(s) to be stored and aqueous solutions of a water-soluble or water-swellable substance which forms a glassy (or possibly rubbery) state on drying.

According to this invention, therefore, we provide a process of rendering a material suitable for storage comprising spraying into a hot gas stream, an aqueous mixture of the material and a carrier substance which is water-soluble or water-swellable, thereby drying the mixture to particles in which the said carrier substance is in a glassy or rubbery state, and separating the particles from the gas stream.

This process is of course also a process for preparing a storable composition.

The aqueous mixture of the material for storage and the carrier substance will generally be formed by mixing the material with the carrier substance in the presence of water. However, it is possible that the material to be stored will be provided as a solution which already contains a substance which is able to form a glass and so is suitable as a carrier substance, so that deliberate addition of a carrier substance is unnecessary.

As will be explained in more detail below it is preferred that the composition produced by the drying procedure displays a glass transition temperature of at least 20° C., preferably at least 30° C. and possibly well above this e.g. at least 50° C.

The invention may be utilised for stable storage of a single material, or for a mixture of materials which have little or no effect on each other.

However, a further possibility is that the invention is used to produce a composition which contains a plurality of materials which (when in contact with water) form part or all of a reacting system. These materials may be fairly simple chemicals.

Yet another possibility is that the material comprises viable biological cells.

Material Stored (i) inanimate materials

The material(s) stabilised for storage may potentially be any of a wide range of materials which are ordinarily liable to undergo chemical reaction, and so are not stable during storage at ambient temperature of 20° C.

One category of materials to which the invention is applicable is proteins and peptides, including derivatives thereof such as glycoproteins. Such proteins and peptides may be any of: enzymes, transport proteins, e.g. haemoglobin, immunoglobulins, hormones, blood clotting factors, other blood plasma components and pharmacologically active proteins or peptides.

Another category of materials to which the invention is applicable comprises nucleosides, nucleotides, dinucleotides, oligonucleotides (say containing up to four nucleotides) and also enzyme cofactors, whether or not these are nucleotides. Enzyme substrates in general are materials to which the invention may be applied.

The material for stabilisation and storage may be isolated from a natural source, animal, plant, fungal or bacterial, may be produced by and isolated from cells grown by fermentation in artificial culture, or may be produced by chemical synthesis. Such cells may or may not be genetically transformed cells.

The material will need to be soluble in aqueous solution, at least to the extent of forming a dilute solution which can be used for incorporation into the carrier substance.

As mentioned above, a possibility is to store more than one component of a reacting system in a glass. This can be useful for materials which will be required to be used together in, for example, an assay or a diagnostic kit.

Storing the materials as a single glassy preparation provides them in a convenient form for eventual use. For instance, if an assay requires a combination of one or more substrates, and/or a cofactor and an enzyme, two or all three could be stored in a glass in the required concentration ratio and be ready for use in the assay.

If multiple materials are stored, they may be mixed together in an aqueous solution and then incorporated together into a glass. Alternatively they may be incorporated individually into separate glasses which are then mixed together.

When multiple materials are stored as a single composition (which may be two glasses mixed together) one or more of the materials may be a protein, peptide, nucleoside, nucleotide or enzyme cofactor. It is also possible that the materials may be simpler species. For instance a standard assay procedure may require pyruvate and NADH to be present together. Both can be stored alone with acceptable stability. However, when brought together in aqueous solution they begin to react. If put together in required proportions in the glassy state they do not react and the glass can be stored.

Material to be Stored (ii) cells

In a significant development of this invention we have found that the material which is stored may comprise viable biological cells. The composition obtained by spray drying can then contain the cells in a state of suspended animation, and viable cells can be recovered from storage. Cells which may be placed in a storable condition by the method of the invention will preferably be existing as single cells, being either a single cell organism or being cells which are in culture as individual, undifferentiated cells. In particular the cells may be a bacterial culture, which may be isolated from nature or may be a laboratory or industrial bacterial strain including genetically transformed bacteria. The cells may be eukaryotic cells, notably including yeasts but also other fungal cultures. Again the cell culture may be a natural isolate or a laboratory or industrial culture produced by fermentation including genetically transformed strains.

The Carrier Substance

A glass is defined as an undercooled liquid with a very high viscosity, that is to say at least $10^{13}$ Pa.s, probably $10^{14}$ Pa.s or more.

Normally a glass presents the appearance of a homogeneous, transparent, brittle solid which can be ground or milled to a powder. In a glass, diffusive processes take place at extremely low rates, such as microns per year. Chemical or biochemical changes involving more than one reacting moiety are practically inhibited.

Above a temperature known as the glass transition temperature $T_g$, the viscosity drops rapidly and the glass turns into a rubber, then into a deformable plastic which at even higher temperatures turns into a fluid.

The carrier substance employed in this invention must be hydrophilic—either water-soluble or water-swellable—so that water will act as a plasticiser. Many hydrophilic materials, both of a monomeric and a polymeric nature either exist in an amorphous state or can be converted into such an amorphous state which exhibit the glass/rubber transitions characteristic of amorphous macromolecules. They have well defined glass transition temperatures $T_g$ which depend on the molecular weight and on molecular complexity of the substance concerned. $T_g$ is depressed by the addition of diluents. Water is the universal plasticiser for all such hydrophilic materials. Therefore, the glass/rubber transition temperature is adjustable by the addition of water or an aqueous solution.

It will generally be preferred to employ a carrier substance which, on its own, forms a glass rather than a rubber at ambient temperature. Hence it will be preferable that the carrier substance, on its own, is able to exist in a glassy amorphous state with a glass transition temperature $T_g$ above 20° C.

Mixtures of substances may be used as carrier substance if the components are miscible as a solid solution. If so, material(s) of lower $T_g$ serve as plasticiser(s) for material(s) of higher $T_g$.

A composition prepared by a process of this invention will generally have a glass transition temperature $T_g$ below that of the pure carrier substance.

If the dried composition is stored in the glassy state (below $T_g$) the deterioration of the active material is retarded to the extent that, on practical time-scales, even substances which in solution are extremely labile are found to possess long shelf-lives.

Full biochemical activity is maintained, but locked in, throughout this period at temperatures below $T_g$ and can be rapidly released by resolubilization of the glass in an aqueous medium.

If the material to be stored is inanimate, then in order to provide a long storage life, it will generally be desirable that the dried composition has a glass transition temperature of at least 20° C. For achieving this it is desirable that the glass-forming carrier substance, when anhydrous or nearly so, displays a glass transition temperature $T_g$ of at least 40° C., better at least 50° C. There is no theoretical upper limit on $T_g$. In practice suitable materials have values of $T_g$ below 250° C., usually below 200° C. A desirable range is therefore 50° to 200° C., preferably 60° or 80° C. to 150° or 180° C.

If the material to be stored comprises biological cells, the composition containing the cells may well be in an amorphous rubbery state. Thus a composition obtained by the method of the invention and comprising biological cells may have a glass transition temperature $T_g$ below 20° C. for instance in the range between 0° C. and 20° C. even though its carrier substance has a glass transition temperature above 20° C. Such compositions could readily be stored with refrigeration to approximately 0° C. so as to be stored in the glassy rather than rubbery state.

If $T_g$ of the final composition made according to the invention is sufficiently high, storage can be at room temperature. However, if $T_g$ of the composition is close to or below room temperature it may be necessary or desirable to refrigerate the composition if storage is for a prolonged period. This is less convenient but still is more economical than freeze-drying.

If a composition is heated above its $T_g$ during storage, it will change to its rubbery state. Even in this condition stored materials are stable for a considerable period of time. Consequently, it may well do no harm if the temperature of a stored composition is allowed to rise above $T_g$ for a limited time, such as during transportation.

If a composition is maintained slightly above its $T_g$ (and therefore in a rubbery condition) the storage life will be limited but still considerable and the benefit of the invention will be obtained to a reduced extent.

Conversely, if $T_g$ of the composition is well above room temperature, the composition is better able to withstand storage at an elevated temperature, e.g. in a hot climate.

The carrier substance should be sufficiently chemically inert towards an inanimate material which is to be incorporated in it. An absolute absence of chemical reactivity may not be essential, as long as it is possible to incorporate the material, store the glass, and recover the material without serious degradation through chemical reaction.

If the material to be stored comprises biological cells, the carrier substance should not be toxic to these cells. Indeed the carrier substance may be a nutrient for the cells and able to support cell division so long as the drying operation is carried out at sufficient rapidity that the carrier substance is not consumed by the cells.

As mentioned above, the carrier substance, which very preferably forms a glass, may be deliberately added to form the mixture which is spray dried. For instance it may be added to a solution of the material to be stored.

Many organic substances and mixtures of substances will form a glassy state on cooling from a melt.

In this context carbohydrates are an important group of glass forming substances: thus candy is a glassy form of sugar (glucose or sucrose). The $T_g$ for glucose, maltose and maltotriose are respectively 31, 43 and 76° C. (L. Slade and H. Levine, Non-equilibrium behaviour of small carbohydrate-water systems, Pure Appl. Chem. 60 1841 (1988)). Water depresses $T_g$ and for these carbohydrates the depression of $T_g$ by small amounts of moisture is approximately 6° C. for each percent of moisture added. We have determined the $T_g$ value for sucrose as 65° C.

In addition to straightforward carbohydrates, other polyhydroxy compounds can be used, such as carbohydrate derivatives and chemically modified carbohydrates (i.e. carbohydrates which have undergone chemical reaction to alter substituents on the carbon backbone of the molecule but without alteration of that backbone).

Another important class of glass forming substances are water-soluble or water-swellable synthetic polymers, such as polyacrylamide.

Yet another class of substances which are suitable are proteins and protein hydrolysates. Thus albumin can be used, and so can hydrolysis products of gelatin.

A group of glass forming substances which may in particular be employed are sugar copolymers described in U.S. Pat. No. 3,300,474 and sold by Pharmacia under the Registered Trade Mark "Ficoll". This U.S. patent describes the materials as having molecular weight 5,000 to 1,000,000 and containing sucrose residues linked through ether bridges to bifunctional groups. Such groups may be alkylene of 2, 3 or more carbon atoms but not normally more than 10 carbon atoms. The bifunctional groups serve to connect sugar residues together. These polymers may for example be made by reaction of the sugar with a halohydrin or a bis-epoxy compound.

The suitability of an intended carrier substance, and the amount of material which can be incorporated into it can both be checked by preparing a glassy or rubbery composition with the material incorporated, and then recovering the material without any substantial period of storage.

$T_g$ values can be determined with a differential scanning calorimeter and can be detected as a point at which a plot of heat input against temperature passes through an inflection point—giving a maximum of the first temperature derivative.

As was also mentioned above, a further possibility is that the material which is to be stored may occur in a form which incorporates a suitable carrier substance. It is envisaged in particular that this situation may arise with products derived from blood plasma where the material to be stored is a relatively minor component of the blood plasma and other components which naturally occur in the blood plasma, notably albumin, are able to form a glass on drying. In such a situation there would be no need for separate addition of a glass-forming carrier substance although the possibility is not ruled out.

Processing

The first stage is to provide an aqueous mixture of the material to be stored and the water-soluble or water-swellable carrier substance. This may be done by mixing the carrier substance, as a powder or as an aqueous solution, with a solution or suspension of the active material to be stored. Alternatively a suitable solution may be available from some other process, without requiring deliberate addition of glass-forming carrier, as mentioned above.

When the invention is applied to the storage of cells, a possibility which has been found suitable for some cells is to suspend the cells in a dilute aqueous solution containing the carrier substance and then subject this to the drying step. To arrive at the suspension, solid carrier material may be dissolved in a suspension of the cells in a dilute aqueous buffer solution. This can lead to a composition with a glass transition temperature above ambient and temperature having very good storage stability.

For some cells, it has been found that survival during drying is better if the cells are dried from a mixture which is rather closer to their normal growth medium. This may for example be carried out by adding carrier substance to an aqueous culture of the cells in their growth medium and drying the resulting mixture. Many bacteriological growth media have a relatively high electrolyte content and this electrolyte or other components is effective to lower the glass transition temperature of the dried product. If this procedure is followed the composition is likely to have a glass transition temperature below ambient temperature making it desirable to store the composition under refrigeration. In this situation the need for refrigerated storage is accepted for the sake of greater survival of cells during the drying operation.

In order to determine whether any cell species can be dried from a simple aqueous suspension or whether it should be dried from something akin to its growth medium, a test can be made by drying some cells by each procedure, then recovering the cells without storing for any substantial period of time and determining the quantity of cells which have survived.

After arriving at a mixture containing the material to be stored and a carrier substance the next step is a spray drying operation in which the above aqueous mixture is sprayed into a hot gas stream. The gas will generally be air but could be some other gas such as nitrogen.

Apparatus to carry out spray drying on a fairly small scale is available from various manufacturers. One is Drytec Ltd, Tonbridge, Kent who manufacture a pilot plant scale dryer. Another manufacturer is Lab-Plant Ltd of Longwood, Huddersfield, England who manufacture a laboratory scale dryer.

BRIEF DESCRIPTION OF THE DRAWING

Process plant to carry out spray drying on a larger scale is also well known.

The sole drawing is a diagrammatic illustration of laboratory scale spray-drying apparatus.

In this apparatus air from the atmosphere is drawn in by a blower 10 and passes over an electric heater 12 after which the air passes down a main chamber 16. The aqueous mixture to be sprayed is drawn up from a supply vessel 18 by means of a peristaltic metering pump 20 and delivered to a spray nozzle 22 which discharges the aqueous mixture as a fine spray into the stream of hot air coming from the heater 12.

The droplets of spray are dried to solid powder form as they pass down within the main chamber 16. The powder is entrained in the air which has passed down the main chamber 16. This leaves by an exit tube 26 at one side delivering to a cyclone separator 28 which serves to remove entrained solid particles from the air stream. The solid particles which are separated from the air stream in this way are collected as the product in a detachable vessel 30 while the air passes out to atmosphere through an exhaust tube 32. Solids which stick to the wall of the main chamber fall into waste container 24.

A significant parameter in the operation of any spray drying apparatus is the temperature of the gas stream which is admitted to the main chamber and into which the spray is delivered. For the present invention this inlet temperature of the gas stream will generally exceed 80° C., will usually exceed 90° C. and may well lie in a range from 100 to 250/300° C.

The aqueous mixture which is delivered into the gas stream may typically contain from 10 up to 50 or even 250 grams per liter of the carrier substance. The content of material to be stored can vary widely but will often lie within a broad range from $10^{-3}\%$ to 10% by weight of the carrier substance. Much lower levels are possible. A substance whose desired activity is present when very dilute might be stored at a concentration as low as $10^{-5}\%$ by weight of the dried composition. By contrast storage at a concentration of stored material of up to 50% by weight or even more can also be envisaged.

In many instances the carrier substance will form at least 20%, better at least 25% or 30% by weight of the particulate composition formed by drying and usually at least 50% by weight of that particulate composition.

The particulate solid compositions produced by discharging an aqueous mixture into a heated gas stream in accordance with the invention will frequently be sufficiently dry for storage without further processing. However it is within the scope of the invention to subject these compositions to further drying such as by subjecting them to sub-atmospheric pressure possibly accompanied by moderate heating so as to reduce any residual moisture content.

When the material to be stored comprises biological cells the moisture content of a composition produced by a method of the invention would typically be in the range 3 to 9% by weight. A low moisture content enhances stability.

The suitability of conditions for preparing a storable composition can be checked by carrying out the preparation but recovering the material without any substantial period of storage and determining the proportion which has survived. As mentioned above storage stability can if desired be tested by storage at a temperature above ambient, although not above the $T_g$ value of the glass.

Recovery from storage

Recovery of stored material from a composition produced by drying in accordance with this invention can be effected by simply adding water or aqueous solution to a quantity of the composition with the active material therein. If the carrier substance is water-soluble the result is a solution of the material and the carrier substance.

Separation by chromatography to isolate a stored, active, inanimate material from the carrier substance is possible. However, in general it will be neither desirable nor necessary. Instead the carrier substance is chosen so that it will not interfere with the use (e.g. an assay) of the stored, active material.

In the case of a water-swellable carrier substance, it will remain out of solution, perhaps as a gel, and the solution of the material can be separated by centrifugation if required.

A further aspect of this invention is use of a composition prepared according to the invention to provide a solution of the stored material, by addition of water or aqueous solution to the composition. The application to which the solution of recovered material is put may or may not be a therapeutic application.

EXAMPLE 1

The active material to be placed in a storable form was lactate dehydrogenase (LDH) type XI (ex rabbit muscle) from Sigma Chemical Co. The glass forming carrier substance employed was Ficoll 400 DL (Pharmacia, Reg. Trade Mark) which is a copolymer of sucrose and epichlorohydrin. It is water-soluble and has a $T_g$ of 97° C.

8 g of Ficoll was added to 200 ml of 0.01 M phosphate buffer pH 7 and stirred at ambient temperature until a clear solution was obtained. This solution was then cooled to, and stored at, 4° C. until use. All solutions were used within 72 hr. To 200 ml of the phosphate buffer/Ficoll solution (at 4° C.) 10 mg of LDH was added. The resulting solution was then passed through a spray-drier (Drytec, pilot scale drier) to give a dry powder containing 1.25 mg LDH/g powder. An air inlet temperature of 210° C. (at the air inlet to the drying chamber) was employed; this produced an air temperature of 70° C. at the entry to the cyclone separator.

The dried material was a particulate solid. This was divided into 2 g portions and placed into vials. The vials were sealed under a normal atmosphere and stored at ambient temperature (fluctuating between 10 and 35° C.). Portions of powder were periodically removed and the vials resealed. Assays were performed following drying, and periodically thereafter. An assay of the solution prior to drying was used as the control.

The actual enzyme activity was determined by the following procedure (Hatley, Franks and Mathias, Process Biochemistry, December 1987 page 170) and based on a minimum of nine replicates. The powder was dissolved in phosphate buffer to give a test solution calculated to contain 1 μg protein per ml (for the control sample a portion of the solution to be dried was taken and diluted to 1 μg per ml).

Activity of the test solution was then measured: 2.7 ml of 0.01 phosphate buffer pH 7, 0.1 ml of 2 mg/ml NADH and 0.1 ml of 10 mM pyruvate were placed into a cuvette of light path 10 mm. The cuvette was capped and shaken. 0.1 ml of the test solution was added and the cuvette again capped and shaken. The absorbance at 340 nm was recorded at 30 s intervals for a total of three minutes. The temperature of the solution was also noted. The absorbance change per minute, δA, was calculated. The enzyme activity was then calculated as follows:

$$LDH \text{ activity (units/mg)} = \frac{\delta A \times TCF}{6.25 \times C}$$

where:
δA=the absorbance change per minute
6.25=a correction factor for the molar absorbance of NADH.
TCF=a temperature correction factor applied to all assays performed at temperatures other than 25° C.
C=the concentration of protein in mg/ml The control (unprocessed) solution had an activity of 322 U/mg protein. This was taken as 100% and all subsequent assays quoted relative to this value. Enzyme activities were:

| Before Drying | Storage period after drying (days) | | | | |
|---|---|---|---|---|---|
| | 0 | 12 | 33 | 91 | 138 |
| 100% | 82% | 83% | 86% | 71% | 100% |

Product $T_g$ was determined throughout the storage period. The value decreased from 79° C. to 64° C. as moisture entered the product as it was repeatedly opened and resealed. However, throughout the experiment the product remained in the form of a glass at the storage temperature.

The results show that enzyme activity was effectively preserved intact through the spray drying procedure and subsequent storage.

EXAMPLE 2

Example 1 was repeated with an air inlet temperature of 130° C. This produced an air temperature of 60° C. at the entry to the cyclone separator. After 138 days storage, enzyme activity was 112% of the control value.

EXAMPLE 3

Example 1 was repeated with two variations. 50 mg of LDH was added to 200 ml of the phosphate buffer/Ficoll solution (at 4° C.). Spray drying gave a dry powder containing 6.25 mg LDH/g powder. Air inlet temperature was 150° C. This produced an air temperature of 70° C. at the entry to the cyclone separator.

After 138 days storage enzyme activity was 117% of the control value.

EXAMPLE 4

The active material was alcohol oxidase from Provesta Enzymes. The glass forming substance employed was Ficoll 400 DL (Pharmacia, Reg. Trade Mark) as used in Example 1.

8 g of Ficoll was added to 200 ml of 0.1 M phosphate buffer pH 7.5 and stirred at ambient temperature until a clear solution was obtained. This solution was then cooled to, and stored at, 4° C. until use. All solutions were used within 72 hr. 100 µg (100 units) of alcohol oxidase was added to 200 ml of the phosphate buffer/Ficoll solution (at 4° C.). The resulting solution was then passed through a spray-drier (Drytec pilot scale drier) to give a dry powder calculated to contain 0.0125 U alcohol oxidase/g powder. An air inlet temperature of 150° C. was employed; this produced an air temperature of 70° C. at the entry to the cyclone separator.

The dried material was divided into 2 g portions and placed into vials. The vials were sealed under a normal atmosphere and stored at ambient temperature (fluctuating between 10 and 35° C.). Portions of powder were periodically removed and the vials resealed. Assays were performed prior to drying and following drying.

As a comparison freeze-dried samples were prepared using principles described in the literature, (F Franks, Cryo-Letters 11, 93–110). 300 mg of Ficoll was dissolved in 20 ml of 0.1 M phosphate buffer pH 7. 1000 units of alcohol oxidase was added to the solution. The solution was divided into 0.2 ml portions in ten 5 ml vials. These were frozen to −30° C. in a small laboratory freeze-drier. A vacuum of 1×10⁻¹ mbar was applied and the samples dried for 24 hr. The vacuum was reduced to its minimum setting of 5×10⁻² mbar and the temperature raised at 5° C./hr to 30° C. After holding the sample at this temperature for two hours the vials were removed and sealed with Bakelite screw-caps. Each vial was calculated to contain 1 unit of enzyme, assuming no activity had been lost during processing. Enzyme activity was assayed before and after freeze drying.

As a further comparison, samples of solution similar to those which were freeze dried, were dried in stationary vials, as described in our published European application EP-A-383569. Enzyme activity was assayed before and after drying.

Assays of enzyme activity were performed as follows: Dried powder was dissolved in phosphate buffer to give a test solution calculated to be 0.1 U per ml (for the control sample a portion of the solution to be dried was taken and serially diluted to 0.1 U per ml).

A stock solution was prepared containing:
- 16 mg 2,2'-azino-di(3-ethylbenzthiazoline-6-sulphonic acid) (ABTS)
- 2 ml absolute ethanol
- 1 ml of 1 mg/ml horseradish peroxidase in distilled water
- All made up to 100 ml with 0.1 M potassium phosphate buffer, pH 7.5.

Another stock solution was:
- 0.1 M potassium phosphate buffer, pH 7.5.

2.5 ml of the ABTS stock solution was pipetted into a 3 ml cuvette, 25 µl of the enzyme solution with an expected activity of 0.1 U alcohol oxidase per ml was added. The cuvette was closed and its contents mixed by inversion. The cuvette was placed in a spectrophotometer and the absorbance change over 3 min at 390 nm recorded.

The absorbance change per minute was determined and multiplied by 3.06 (the extinction coefficient plus the cuvette dilution factor) to give the concentration of enzyme in the solution. Activity retention was calculated by dividing the measured value by 0.1 (the expected activity in the solution) and multiplying by 100 to give a percentage.

It was found that after drying the activity as a percentage of that before drying was:

| | |
|---|---|
| Freeze drying | 35% |
| Drying in stationary vial | 38% |
| Spray drying | 52% |

Suppliers' catalogues show that commercial freeze drying of alcohol oxidase reduces activity to 25%.

The spray dried and freeze dried alcohol oxidase were stored at 35° C. and activity was assessed at intervals. The freeze dried material lost all activity in 20 days. After 30 days the spray dried material retained 90% of its activity assayed directly after spray drying.

EXAMPLE 5

Example 1 was repeated, replacing Ficoll with Byco A which is a cold water soluble protein obtained from gelatin by enzymic hydrolysis. It has a $T_g$ value of 126° C. Byco A is available from Croda Colloids Ltd, Widnes, Cheshire, England.

As in Example 1 enzyme activity was measured both directly following drying and after a period of storage. The measured values of enzyme activity were 88% directly following drying and 113% after 103 days storage at ambient temperature.

EXAMPLE 6

As in Example 1, the active material was lactate dehydrogenase (LDH) type XI and the glass forming substance was Ficoll 400 DL.

10 g of Ficoll was added to 100 ml of 0.01 M phosphate buffer pH 7 and stirred at ambient temperature until a clear solution was obtained. This solution was then cooled to, and stored at, 4° C. until use. All solutions were used within 72 hr. 10 mg of LDH was added to 200 ml of the phosphate buffer/Ficoll solution (at 4° C.). The solution was then passed through a spray-drier (Lab-Plant SD-04) to give a dry powder containing 1 mg LDH/g powder. An air inlet temperature of 170° C. was employed; this produced an air outlet temperature of 75° C. The dried material was sealed in a collection bottle in a normal atmosphere. The samples were stored at ambient temperature (fluctuating between 10 and 35° C.). Portions of powder were periodically removed and assays performed as for Example 1.

Enzyme activities were:

| Before | Storage period (days) | |
|---|---|---|
| Drying | 0 | 61 |
| 100% | 91% | 103% |

EXAMPLE 7

This example describes converting biological cells into a storable composition by a method embodying the invention and then recovering the cells after varying periods of time.

The amount of aqueous solution used in recovery of cells was chosen such that, if there was survival of every cell, the concentration of cells in the recovered suspension would be the same as in the initial suspension before drying. The concentrations of viable cells in these suspensions, before drying and after recovery, were assayed by using a standard quantity of the suspension to make an agar plate. The plate is then incubated and the number of growing colonies was counted.

5 g Ficoll 400 DL (Pharmacia, Reg Trade Mark) was dissolved in 100 ml growth medium. 5 ml *Lactobacillus bulgaricus* cells in growth medium were added to the Ficoll solution to give a cell suspension of approximately 1×107 cells/ml. The suspension was then spray dried, using a laboratory scale spray drier, (Lab-Plant SD-04), with input temperature 190° C. and output temperature 104° C., and collected as a dry powder. The powder was immediately dispensed into several small vials and the vials were capped and stored at 4° C.

Viability testing:

Before drying (control):

0.5 ml cell suspension was transferred to a sterile tube containing 9.5 ml sterile growth medium. Serial dilutions were made in the manner of Miles and Misra. 1 ml cell suspension from an appropriate dilution was transferred to a 9 cm sterile petri dish and mixed with 10 ml molten growth medium at approximately 37° C. The agar plate was then allowed to set and incubated for 48 h at 35° C. The colony forming units were then counted.

After drying:

0.5 ml growth medium was added to 0.049 g dried powder (calculated weight of solids in 0.5 ml original cell suspension) and left to stand at room temperature for 30 min to ensure full rehydration. The assay was continued as described above and the number of colony forming units was compared to the number found in the sample assayed before drying.

Further dried samples were assayed at intervals.

| | Results: | |
|---|---|---|
| Storage time | Cfu's in $10^{-5}$ dilution | % of control |
| Before drying (control) | 1365 | |
| Directly after drying | 344 | 25 |
| 2 weeks | 345 | 25 |
| 4 weeks | 319 | 23 |

EXAMPLE 8

5 g Dextrin 10 (maltodextrin, ex Fluka) was dissolved in 100 ml 10% skimmed milk solution. 5 ml *Lactobacillus bulgaricus* cells in growth medium were then added to the solution to give a cell suspension of approximately 1×107 cells/ml. The suspension was then spray dried, using a laboratory scale spray drier, (Lab-Plant SD-04), with input temperature 160° C. and output temperature 89° C., and collected as a dry powder. The powder was immediately dispensed into several small vials and the vials were capped and stored at 4° C.

Viability testing was carried out as in the previous Example. For testing after drying 0.5 ml growth medium was added to 0.076 g dried powder as the calculated weight of solids in 0.5 ml of the original cell suspension.

| | Results: | |
|---|---|---|
| Storage time | Cfu's in $10^{-5}$ dilution | % of control |
| Before drying (control) | 1321 | |
| Directly after drying | 543 | 41 |
| 2 weeks | 551 | 42 |
| 4 weeks | 392 | 30 |

The moisture content of the spray dried powder was measured by a Karl Fischer coulometric method and found to be 5.2%.

EXAMPLE 9

5 g raffinose was dissolved in 100 ml growth medium. 5 ml *Lactobacillus bulgaricus* cells in growth medium were added to the solution to give a cell suspension of approximately 1×107 cells/ml. The suspension was then spray dried, using a laboratory scale spray drier, (Lab-Plant SD-04), with input temperature 190° C. and output temperature 108° C., and collected as a dry powder. The powder was immediately dispensed into several small vials and the vials were capped and stored at 4° C.

Viability testing was carried out as in Example 7.

| Storage time | Cfu's in $10^{-5}$ dilution | % of control |
|---|---|---|
| Before drying (control) | 1620 | |
| Directly after drying | 127 | 8 |
| 2 weeks | 174 | 11 |
| 4 weeks | 176 | 11 |
| 8 weeks | 117 | 7 |

EXAMPLE 10

5 g sodium glutamate was dissolved in 100 ml growth medium. 5 ml *Lactobacillus bulgaricus* cells in growth medium were added to the solution to give a cell suspension of approximately 1×10⁷ cells/ml. The suspension was then spray dried, using a laboratory scale spray drier, (Lab-Plant SD-04), with input temperature 190° C. and output temperature 114° C., and collected as a dry powder. The powder was immediately dispensed into several small vials and the vials were capped and stored at 4° C.

Viability testing was carried out as in Example 7.

| Storage time | Cfu's in $10^{-5}$ dilution | % of control |
|---|---|---|
| Before drying (control) | 1472 | |
| Directly after drying | 515 | 35 |
| 2 weeks | 516 | 35 |
| 4 weeks | 534 | 36 |
| 8 weeks | 451 | 31 |

What is claimed is:

1. A storage-stable composition of spray-dried particles comprising:
   an active material selected from the group consisting of proteins, peptides, nucleosides, nucleotides, dinucleotides, oligonucleotides, and viable biological cells, and
   a protein or protein hydrolysate carrier substance that is water-soluble or water-swellable, and that, on its own, is able to exist in a glassy state with a glass transition temperature (Tg) above 20° C.,
   wherein (i) the particles have a Tg above 30° C., (ii) the carrier is in a glassy state, and (iii) a storage stable composition is characterized as one which, when stored at ambient temperature for a period of 30 days, maintains at least about 90% of its initial activity or chemical identity measured directly after spray drying.

2. The composition of claim 1, comprising particles having a Tg above 50° C.

3. The composition of claim 1, wherein the carrier substance comprises at least 20% by weight of the composition.

4. The composition of claim 1, where the carrier substance, when on its own, is able to exist in a glassy state with a glass transition temperature in the range from 60° C. to 180° C.

5. The composition of claim 1, further comprising a polyhydroxy carrier substance.

6. The composition of claim 5, wherein the polyhydroxy carrier substance is a carbohydrate.

7. The composition of claim 1, comprising at least 25% by weight carrier substance.

8. The composition of claim 1, comprising at least 30% by weight carrier substance.

9. The composition of claim 1, comprising at least 50% by weight carrier substance.

10. The composition of claim 1, wherein said carrier substance, when anhydrous, displays a Tg of at least 40° C.

11. The composition of claim 1, wherein said carrier substance, when anhydrous, displays a Tg of at least 50° C.

12. The composition of claim 6, wherein said polyhydroxy carrier substance is a sugar.

13. The composition of claim 1, wherein said active material comprises a protein or a peptide.

14. The composition of claim 1, wherein said active material is selected from the group consisting of nucleosides, nucleotides, dinucleotides, and oligonucleotides.

15. The composition of claim 1, wherein said active material comprises biological cells.

16. The composition of claim 1 having a moisture content of from about 3% to 9% by weight.

17. The composition of claim 10, wherein said active material comprises a protein or a peptide.

18. The composition of claim 11, wherein said active comprises a protein or a peptide.

19. The composition of claim 1, wherein said carrier substance comprises gelatin or a hydrolysis product of gelatin.

20. A storage-stable composition of spray-dried particles comprising:
   an active material selected from the group consisting of nucleosides, nucleotides, dinucleotides, oligonucleotides, and viable biological cells, and
   a carrier substance that is water-soluble or water-swellable, and that, on its own, is able to exist in a glassy state with a glass transition temperature (Tg) above 20° C.,
   wherein (i) the particles have a Tg above 30° C., (ii) the carrier is in a glassy state, and (iii) a storage stable composition is characterized as one which, when stored at ambient temperature for a period of 30 days, maintains at least about 90% of its initial activity or chemical identity measured directly after spray drying.

21. The composition of claim 20, wherein said active material is selected from the group consisting of nucleosides, nucleotides, dinucleotides, and oligonucleotides.

22. The composition of claim 21, wherein said active material comprises a nucleoside.

23. The composition of claim 21, wherein said active material comprises a nucleotide.

24. The composition of claim 21, wherein said active material comprises an oligonucleotide.

25. The composition of claim 20, wherein said active material comprises viable biological cells.

26. The composition of claim 21, comprising particles having a Tg above 50° C.

27. The composition of claim 21, wherein the carrier substance comprises at least 20% by weight of the composition.

28. The composition of claim 21, where the carrier substance, when on its own, is able to exist in a glassy state with a glass transition temperature in the range from 60° C. to 180° C.

29. The composition of claim 21, wherein the carrier substance is a polyhydroxy compound.

30. The composition of claim 21, wherein the carrier substance is a carbohydrate.

31. The composition of claim 21, comprising at least 25% by weight carrier substance.

32. The composition of claim 21, comprising at least 30% by weight carrier substance.

33. The composition of claim 21, comprising at least 50% by weight carrier substance.

34. The composition of claim 21, wherein said carrier substance, when anhydrous, displays a Tg of at least 40° C.

35. The composition of claim 21, wherein said carrier substance, when anhydrous, displays a Tg of at least 50° C.

36. The composition of claim 30, wherein said carrier comprises a sugar.

37. The composition of claim 25, comprising particles having a Tg above 50° C.

38. The composition of claim 25, wherein the carrier substance comprises at least 20% by weight of the composition.

39. The composition of claim 25, where the carrier substance, when on its own, is able to exist in a glassy state with a glass transition temperature in the range from 60° C. to 180° C.

40. The composition of claim 25, wherein the carrier substance is a polyhydroxy compound.

41. The composition of claim 25, wherein the carrier substance is a carbohydrate.

42. The composition of claim 25, comprising at least 25% by weight carrier substance.

43. The composition of claim 25, comprising at least 30% by weight carrier substance.

44. The composition of claim 25, comprising at least 50% by weight carrier substance.

45. The composition of claim 25, wherein said carrier substance, when anhydrous, displays a Tg of at least 40° C.

46. The composition of claim 25, wherein said carrier substance, when anhydrous, displays a Tg of at least 50° C.

47. The composition of claim 25, wherein said carrier comprises a sugar.

48. The composition of claim 25 having a moisture content of from about 3% to 9% by weight.

49. A storage-stable composition of spray-dried particles comprising:

an active material selected from the group consisting of proteins, peptides, nucleosides, nucleotides, dinucleotides, oligonucleotides, and viable biological cells, and a carrier substance that is water-soluble or water-swellable, and that, on its own, is able to exist in a glassy state with a glass transition temperature (Tg) above 20° C., wherein (i) the particles have a Tg above 30° C., (ii) the carrier is in a glassy state, (iii) the composition has a moisture content from about 3% to 9% by weight, and (iv) a storage stable composition is characterized as one which, when stored at ambient temperature for a period of 30 days, maintains at least about 90% of its initial activity or chemical identity measured directly after spray drying.

50. The composition of claim 49, wherein the carrier substance comprises at least 20% by weight of the composition.

51. The composition of claim 49, where the carrier substance, when on its own, is able to exist in a glassy state with a glass transition temperature in the range from 60° C. to 180° C.

52. The composition of claim 49, wherein the carrier substance is a polyhydroxy compound.

53. The composition of claim 52, wherein the carrier substance is a carbohydrate.

54. The composition of claim 49, comprising at least 25% by weight carrier substance.

55. The composition of claim 49, comprising at least 30% by weight carrier substance.

56. The composition of claim 49, comprising at least 50% by weight carrier substance.

57. The composition of claim 49, wherein said carrier substance, when anhydrous, displays a Tg of at least 40° C.

58. The composition of claim 49, wherein said carrier substance, when anhydrous, displays a Tg of at least 50° C.

59. The composition of claim 53, wherein said carrier comprises a sugar.

60. The composition of claim 57, wherein said active material comprises a protein or a peptide.

61. The composition of claim 58, wherein said active material comprises a protein or a peptide.

* * * * *